(12) United States Patent
Cheon et al.

(10) Patent No.: US 11,371,064 B2
(45) Date of Patent: Jun. 28, 2022

(54) TRANSFORMED YEAST PRODUCING NOVEL 1-OCTEN-3-OL, AND PREPARATION METHOD THEREFOR

(71) Applicants: KYONGSANGBUK-DO, Andong-si (KR); KYUNGPOOK NATIONAL UNIVERSITY INDUSTRY-ACADEMIC COOPERATION FOUNDATION, Daegu (KR)

(72) Inventors: Woo Jae Cheon, Pohang-si (KR); Kwang Seon Lee, Gyeongju-si (KR); Sang Wung Kim, Gyeongju-si (KR); Jong-Guk Kim, Daegu (KR); Nan Yeong Lee, Daegu (KR); Minji Jeong, Pohang-si (KR)

(73) Assignees: KYONGSANGBUK-DO, Andong-si (KR); KYUNGPOOK NATIONAL UNIVERSITY INDUSTRY-ACADEMIC COOPERATION FOUNDATION, Daegu (KR)

(*) Notice: Subject to any disclaimer, the term of this patent is extended or adjusted under 35 U.S.C. 154(b) by 0 days.

(21) Appl. No.: 16/971,582

(22) PCT Filed: Feb. 21, 2019

(86) PCT No.: PCT/KR2019/002125
§ 371 (c)(1),
(2) Date: Aug. 20, 2020

(87) PCT Pub. No.: WO2019/164294
PCT Pub. Date: Aug. 29, 2019

(65) Prior Publication Data
US 2021/0002674 A1  Jan. 7, 2021

(30) Foreign Application Priority Data

Feb. 21, 2018 (KR) .................. 10-2018-0020608
Feb. 19, 2019 (KR) .................. 10-2019-0019496

(51) Int. Cl.
| | | |
|---|---|---|
| *C12P 7/04* | (2006.01) | |
| *C12N 1/16* | (2006.01) | |
| *C12N 9/02* | (2006.01) | |
| *C12N 9/88* | (2006.01) | |
| *C12N 1/18* | (2006.01) | |
| *C12R 1/865* | (2006.01) | |

(52) U.S. Cl.
CPC .............. *C12P 7/04* (2013.01); *C12N 1/16* (2013.01); *C12N 9/0069* (2013.01); *C12N 9/88* (2013.01); *C12N 1/185* (2021.05); *C12R 2001/865* (2021.05); *C12Y 113/11* (2013.01); *C12Y 402/99* (2013.01)

(58) Field of Classification Search
None
See application file for complete search history.

(56) References Cited

U.S. PATENT DOCUMENTS

| | | | |
|---|---|---|---|
| 6,238,898 B1 | 5/2001 | Häusler et al. | |
| 2006/0156430 A1* | 7/2006 | McGonigle | C12N 9/0077 800/278 |
| 2010/0313309 A1* | 12/2010 | Metz | A61P 15/06 800/295 |

FOREIGN PATENT DOCUMENTS

| | | |
|---|---|---|
| KR | 10-2013-0100141 A | 9/2013 |
| KR | 10-2014-0087843 A | 7/2014 |
| KR | 10-2014-0092284 A | 7/2014 |
| KR | 10-1446315 B1 | 9/2014 |
| KR | 10-1455204 B1 | 10/2014 |
| WO | WO 2015/176006 A2 | 11/2015 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
International Search Report (PCT/ISA/210) issued in PCT/KR2019/002125, dated Jun. 17, 2019.

* cited by examiner

*Primary Examiner* — Christian L Fronda
(74) *Attorney, Agent, or Firm* — Birch, Stewart, Kolasch & Birch, LLP

(57) ABSTRACT

The present application relates to a method for preparing transformed yeast producing 1-octen-3-ol, and yeast prepared by the method, and is useful in the cosmetic industry and the food development industry which use a *Tricholoma matsutake* scent.

7 Claims, 5 Drawing Sheets

Specification includes a Sequence Listing.

(A) M: DNA ladder marker
1: pYES3/CT (5,870 bp)
2: pYES3/CT + LOX1 (9,034 bp)
3: pYES3/CT + LOX2 (9,145 bp)
4: pYES3/CT + LOX3 (9,730 bp)

(B) M: DNA ladder marker
1: pYES2/CT (5,963 bp)
2: pYES2/CT + HPL (7,528 bp)

TRANSFORMED YEAST PRODUCING NOVEL 1-OCTEN-3-OL, AND PREPARATION METHOD THEREFOR

REFERENCE TO SEQUENCE LISTING SUBMITTED VIA EFS-WEB

This application includes an electronically submitted sequence listing in .txt format. The .txt file contains a sequence listing entitled "3884-0208PUS1_ST25.txt" created on Sep. 1, 2020 and is 18,187 bytes in size. The sequence listing contained in this .txt file is part of the specification and is hereby incorporated by reference herein in its entirety.

TECHNICAL FIELD

The present application relates to a transformed yeast producing 1-octen-3-ol and a method for producing the same.

BACKGROUND ART

*Saccharomyces cerevisiae* was discovered by Leeuwenhoek in 1683 and is a representative yeast belonging to ascomycetes. Yeasts are used in feed because the yeast itself is used as cheap fat and protein sources. Some yeasts are rich in a vitamin B group and also contain vitamin D, and have been used even in the pharmaceutical industry. The yeast was first observed by the inventor of the microscope, Anton van Leeuwenhoek, and brewer's yeast was found in 1680. However, the biological significance of yeast fermentation was known in 1861, and Louis Pasteur first established that wine fermentation was caused by yeasts.

Octenol (1-octen-3-ol), known as matsutakeol, which is one of major flavor components of pine mushrooms, was known to be involved in lipoxygenase and hydroperoxide lyase enzymes during biosynthesis. The octenol (1-octen-3-ol) is a secondary alcohol derived from 1-octen, and exists in the form of two enantiomers of (R)-(−)-1-octen-3-ol and (S)-(+)-1-octen-3-ol. The (R)-(−)-1-octen-3-ol has a fruit flavor and a unique good flavor of pine mushrooms, but the (S)-(+)-1-octen-3-ol has fusty musty odor, weed odor, and artificial odor. Therefore, the (R)-(−)-1-octen-3-ol is known as a major flavor component of pine mushrooms. Linoleic acid of pine mushroom as a substrate is oxidized to (S)-1-hydroperoxy-(8E,12Z)-8,12-octadecadienoic acid (10-HPODE) in fruiting bodies, and in this process, lipoxygenase is involved. In addition, the 10-HPODE is used to biosynthesize (R)-(−)-1-octen-3-ol and 10-Oxo-trans-8-decenoic acid (ODA) again, and an enzyme involved in this process is known as hydroperoxide lyase.

Until now, as a result of expressing genes of lipoxygenase and hydroperoxide lyase of pine mushrooms in the yeast *Saccharomyces cerevisiae* using a plasmid vector, not a chemically synthesizing method, studies on a biosynthesis method of octenol by confirming that octenol (1-octen-3-ol) has been biosynthesized are insufficient. Since the pine mushrooms are edible mushrooms having a very high preference, particularly, in Asia, a transformed yeast that biosynthesizes octenol (1-octen-3-ol) is expected to have a positive effect on related industries such as food development using a pine mushroom flavor.

A conventionally known or common method for producing octenol (1-octen-3-ol) is disclosed in Korean Patent Publication No. 10-2013-0100141. Here, there is disclosed only a chemical production method of synthesizing octenol by hydrogenating 6-methyl-5-hepten-2-one (MH) to 6-methyl-2-heptanone (MHA), reacting with acetylene to form 3,7-dimethyl-1-octine-3-ol (DMOI), and then hydrogenating the DMOI to 3,7-dimethyl-1-octen-3-ol (DMOE). In addition, in Korean Patent Registration Nos. 10-1446315 and 10-1455204, there are only disclosed genes for each lipoxygenase and hydroperoxide lyase involved in the biosynthesis of octenol derived from pine mushrooms, respectively.

Under this background, the present inventors have completed the present application by taking a lot of studies for developing a method for producing octenol (1-octen-3-ol) using yeasts.

DISCLOSURE

Technical Problem

An object of the present application is to provide a transformed yeast for producing 1-octen-3-ol transformed with a recombinant vector comprising a base sequence encoding lipoxygenase and a base sequence encoding hydroperoxide.

Another object of the present application is to provide a method for producing a transformed yeast for producing 1-octen-3-ol.

Yet another object of the present application is to provide a method for producing 1-octen-3-ol.

Other objects and advantages of the present application will be more apparent by the following detailed description in addition to the appended claims and the accompanying drawings. Contents not described in the present specification can be sufficiently recognized and inferred by those skilled in the art or similar art of the present invention, and thus, the description thereof will be omitted.

Technical Solution

Hereinafter, the contents of the present application will be described below in detail. On the other hand, the description and embodiments of one aspect disclosed in the present application may also be applied to the description and embodiments of other aspects with respect to common matters. In addition, all combinations of various components disclosed in the present application belong to the scope of the present application. Further, the specific description described below may not limit the scope of the present application.

In order to achieve the objects of the present application, the present application provides a transformed yeast for producing 1-octen-3-ol transformed with a recombinant vector comprising a base sequence encoding lipoxygenase and a base sequence encoding hydroperoxide.

According to an aspect of the present application, there is provided a method for producing a transformed yeast for producing 1-octen-3-ol comprising the steps of: isolating total RNA of pine mushroom and synthesizing cDNA; PCR-amplifying a lipoxygenase gene and a hydroperoxide lyase gene from the synthesized cDNA; gene-cloning each of the amplified lipoxygenase gene and hydroperoxide lyase gene in a vector; gene-cloning each of the cloned lipoxygenase gene and hydroperoxide lyase gene in each yeast expression vector; and transforming and incubating the yeast expression vector into a yeast to confirm the biosynthesis of 1-octen-3-ol.

As an embodiment of the present application, the present application provides a method for producing a transformed yeast for producing 1-octen-3-ol comprising gene-cloning lipoxygenase-1, 2, and 3 genes consisting of base sequences of SEQ ID NOS: 9, 10, and 11, respectively, and a hydroperoxide lyase gene consisting of a base sequence of SEQ ID NO: 12 and transforming and incubating a recombinant vector comprising the cloned genes into a yeast to confirm the biosynthesis of 1-octen-3-ol. In addition, homologues of the base sequence are included within the scope of the present application. Specifically, the gene homologues may include base sequences having sequence homology of 70% or more, more preferably 80% or more, much more preferably 90% or more, and most preferably 95% or more with the base sequences of the sequence numbers of the present application. The "% of sequence homology" to polynucleotide is determined by comparing two optimally aligned sequences with a comparison region, wherein a part of a polynucleotide sequence in the comparison region may include addition or deletion (i.e., gap) compared with a reference sequence (without including addition or deletion) for the optimal alignment of the two sequences.

According to an aspect of the present application, the present application provides a method for producing 1-octen-3-ol comprising the steps of: biosynthesizing 1-octen-3-ol by incubating the transformed yeast for producing the 1-octen-3-ol of claim 1 in a medium; and obtaining the biosynthesized 1-octen-3-ol.

The term "primer" has a length of 18 to 35 mer at a nucleic acid site having 70% or more of interspecies sequence homology as a result of sequence homology of a gene determined through analysis, and preferably an algorithm of determining a primer sequence in which a sense primer and an antisense primer are not hybridized with each other and the gene and the primer are hybridized with each other under stringent conditions, but is not limited thereto.

The term "polymerase chain reaction (PCR)" is a nucleic acid amplification method that includes a repeated cycle of denaturation of double-stranded DNA, annealing of oligonucleotide primers to a DNA template, and primer extension by DNA polymerase (Mullis et al., U.S. Pat. Nos. 4,683,195, 4,683,202 and 4,800,159; Saiki et al, 1985). The oligonucleotide primer used in PCR is designed to be annealed to an opposite strand of DNA, and a DNA polymerase extension product of the primer acts as a template strand for the other primer. The PCR amplification process results in an exponential increase in a DNA sequence, and the length of the amplified DNA sequence is determined by a 5'-terminal of the oligonucleotide primer.

The term "vector" is used to refer to a DNA fragment(s), and a nucleic acid molecule, which are delivered into a cell. The vector may replicate DNA and be reproduced independently in host cells. The term "carrier" is often used interchangeably with the "vector". The vector may be used as a cloning vector, and the cloning vector is stably maintained in a host and has a use to insert a foreign DNA fragment. Therefore, the vector needs to have a feature capable of being easily inserted or removed when the vector and the foreign DNA are treated with a restriction enzyme. The cloning vector to be used is appropriately selected in consideration of conditions of the characteristics of the gene to be inserted and the characteristics of the restriction enzyme, but preferably, a pGEM easy vector is used in the present application. The term "yeast expression vector" includes a promoter gene, a gene encoding a target protein from which translation initiation and termination codons have been removed, and a terminator, and the promoter gene is preferably a gene selected from the group consisting of GAPDH, PGK, ADH, PHOS, GAL1, and GAL10, but is not limited thereto. The yeast expression vector may be both an integrative yeast plasmid (YIp) and an extrachromosomal plasmid vector. The extrachromosomal plasmid vector is divided into an episomal yeast plasmid (YEp), a replicative yeast plasmid (YRp), and a yeast centromer plasmid (YCp). Furthermore, artificial yeast chromosomes (YACs) can be also used as expression vectors according to the present application. In addition, a particularly preferable yeast vector is a yeast replication plasmid that contains a replication origin ori and an antibiotic resistance cassette to be proliferated and selected in *E. coli*. Furthermore, the yeast vectors have an ARS sequence to be replicated independently regardless of chromosomes in yeast cells, such as HARS1 from *H. polymorpha*, and a metabolic yeast selectable marker, such as URA3 or HLEU2. In the present application, as the yeast expression vector, various vectors may be used, and specifically, a pKLAC2 vector, a Gateway pYES-DEST52 vector, a pAO815 *Pichia* Expression vector, a pYES2/3/CT vector, preferably a pYES3/CT vector or a pYES2/CT vector may be used. The combinations of vectors used to express each gene may be appropriately selected according to a gene to be expressed, its protein, and an amount of the corresponding protein to adjust a ratio thereof. In the present application, specifically, the ratio of 1:5, 1:4, 1:3, 1:2, and 1:1 may be used, preferably, the pYES3/CT vector and the pYES2/CT vector may be used in a ratio of 1:1.

The term "gene cloning" in the present application means a technique of making the same gene group in large quantities by binding a target gene to a vector having self-replicating ability, such as a plasmid, a phage, a cosmid, etc., and introducing and proliferating the bound vector into various hosts such as *E. coli*, yeast, etc. Cloning and subcloning in *E. coli* are performed by binding a target gene amplified by a polymerase chain reaction (PCR) method, etc., to a vector having a replication origin and an antibiotic selectable marker using a DNA ligase, introducing the bound vector into cells such as *E. coli*, yeast, or the like, and then examining antibiotic resistance to screen the cloned cells.

The term "yeast" in the present application may be yeasts belonging to *Saccharomyces, Schizosaccharomyces, Sporobolomyces, Torulopsis, Tricosporon, Wickerhamia, Ashbya, Blastomyces, Candida, Citeromyces, Crebrothecium, Cryptococcus, Debaryomyces, Endomycopsis, Geotrichum, Hansenula, Kloeckera, Lipomyces, Pichia, Rhodosporidium* or *Rhodotorula* genus, more preferably yeasts belonging to *Saccharomyces* and *Schizosaccharomyces*, most preferably *Saccharomyces cerevisiae*. An appropriate type of yeast may be selected and used according to an expression rate of a gene and an amount and efficiency of a product to be finally expressed. The transformed yeasts of the present application, *Saccharomyces cerevisiae* KMG 1801, KMG 1802, and KMG 1803 were deposited with deposit numbers KCTC13476BP, KCTC13477BP, and KCTC13478BP in the Korea Collection for Type Cultures (KCTC) on Feb. 6, 2018, respectively.

For example, when a host cell is yeast, promoters available in the expression construct include a GAL10 promoter, a GAL1 promoter, an ADH1 promoter, an ADH2 promoter, a PHO5 promoter, a GAL1-10 promoter, a TDH3 promoter, a TDH2 promoter, a TDH1 promoter, a PGK promoter, a PYK promoter, an ENO promoter, a T7 promoter, and a TPI promoter, but are not limited thereto. The promoter may be appropriately selected and used according to a condition, such as an expression rate of a gene and an amount and expression efficiency of a product to be finally expressed.

In the method according to an embodiment of the present application, the method of incubating the transformed host cell may use general methods known in the art, but is not limited thereto. The "transformation" of the yeast allows nucleic acid molecules or vectors to be introduced into cells by standard methods known to those skilled in the art, preferably, electroporation, chemical transformation, transformation by protoplasmic fusion, or particle bombardment. (See: Current Protocols in Molecular Biology, John Wiley & Sons, Edited by: Fred M. Ausubel et al.; Molecular Cloning: A Laboratory Manual (Third Edition), J. Sambrook and D. Russell, 2001, Cold Spring Harbor Laboratory Press). According to a preferred embodiment of the present application, the transformed yeast of the present application was produced using a S.c. EasyComp Transformation kit.

As an embodiment of the present application, there is provided a method for producing 1-octen-3-ol comprising the steps of: biosynthesizing 1-octen-3-ol by incubating the transformed yeast for producing the 1-octen-3-ol of claim 1 in a medium; and obtaining the biosynthesized 1-octen-3-ol.

In the incubation of the yeast of the present application, in order to confirm the biosynthesis of 1-octen-3-ol, the transformed yeast is inoculated into a SC selectable medium in which tryptophan and uracil are deleted, pre-incubated overnight, and then centrifuged to collect the yeast. The collected yeast is inoculated in an SC induction medium in which tryptophan and uracil are deleted, added with 2% Tween-20 and linoleic acid, and then incubated for 20 hours at 30° C. In the present application, preferably, a concentration of linoleic acid as a substrate may be 0.01 to 0.1 M, more preferably 0.5 to 100 mM, and most preferably 3 mM. In addition, in the present application, an incubation temperature is preferably 15° C. to 40° C., more preferably 30° C., and an incubation time is 12 to 48 hours, specifically 18 to 36 hours, 20 to 26 hours, and most preferably 24 hours.

Advantageous Effects

According to the present application, there are excellent effects of being effective in mass production of eco-friendly and economical octenol and contributing to development of foods and cosmetics using a pine mushroom flavor by providing the transformed yeast biosynthesizing 1-octen-3-ol and the method for producing the same.

DESCROPTION OF DRAWINGS

Figure 6:
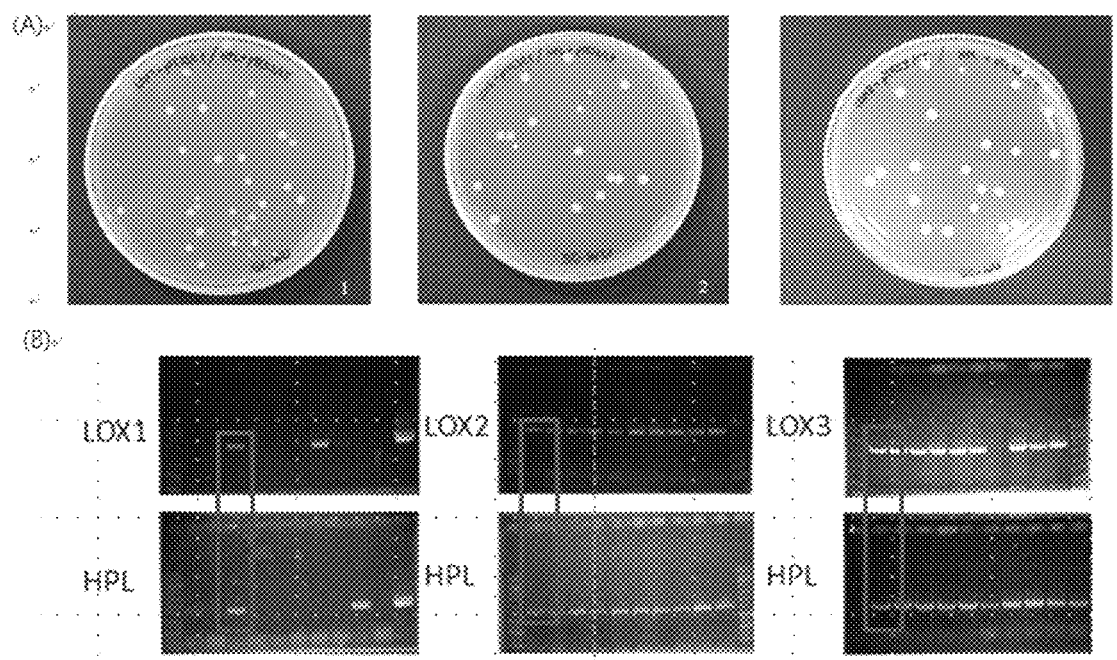

FIG. 6(A) is a photograph of a plate in which transformed yeasts into which a lipoxygenase-1 gene, a lipoxygenase-2 gene, a lipoxygenase-3 gene, and a hydroperoxide lyase gene are introduced are incubated. FIG. 6(B) is an electrophoretic photograph showing colony PCR results of transformed yeasts into which a lipoxygenase-1 gene, a lipoxygenase-2 gene, a lipoxygenase-3 gene, and a hydroperoxide lyase gene are introduced are introduced.

Figure 7:
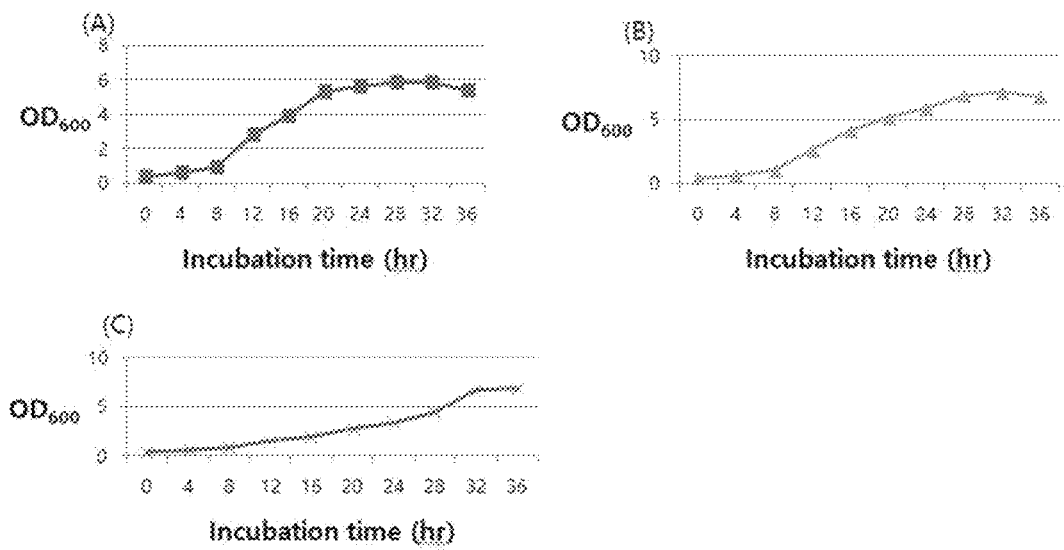

FIG. 7 is a graph showing a growth curve of each yeast transformed with combinations of a lipoxygenase-1 gene, a lipoxygenase-2 gene, a lipoxygenase-3 gene, and a hydroperoxide lyase gene.

Figure 8:
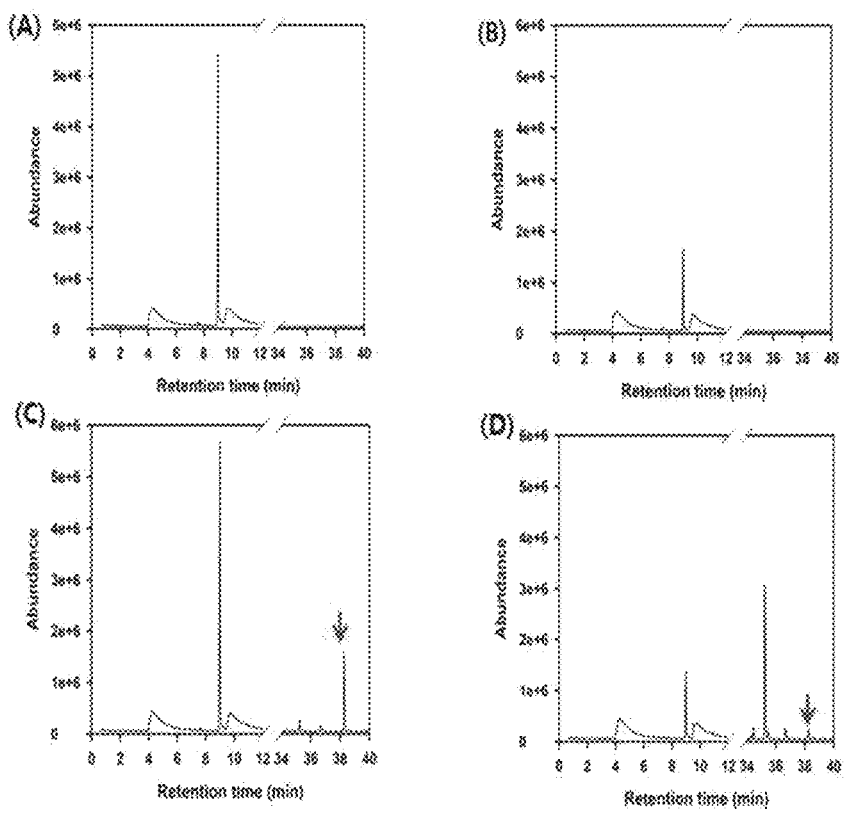

FIG. 8 is a graph showing biosynthesis of 1-octen-3-ol in (A) lysates of cells incubated without adding a substrate, (B) a medium incubated without adding a substrate, (C) lysates of cells incubated by adding a substrate, and (D) a medium incubated by adding a substrate.

Figure 9:
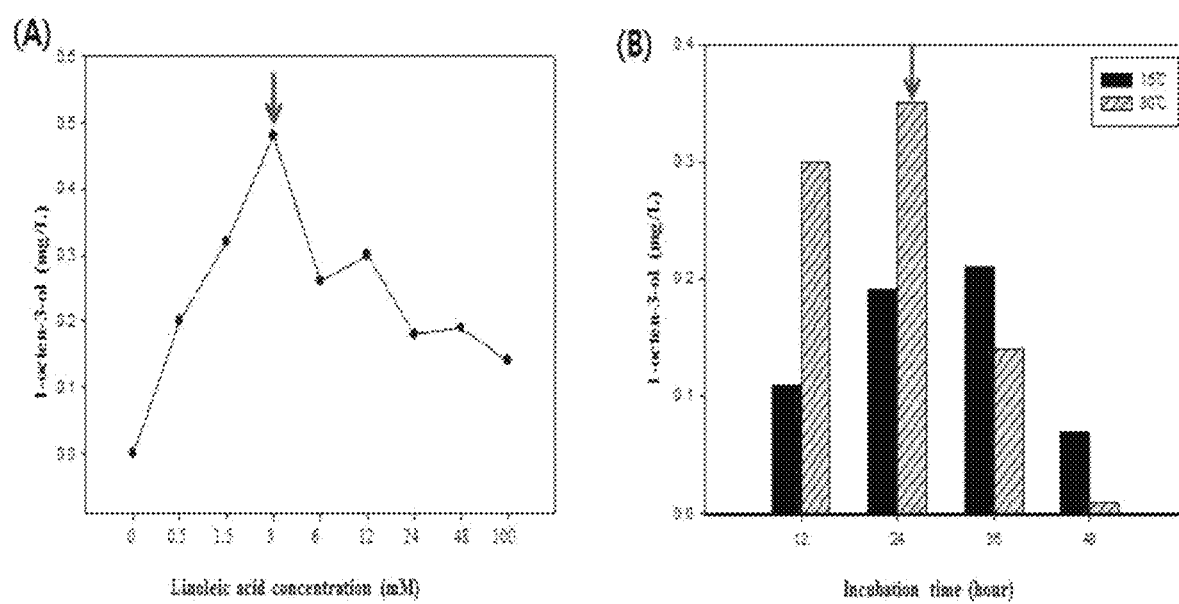

FIG. 9 is a graph showing (A) a biosynthesis amount of 1-octen-3-ol according to a linoleic acid addition concentration and (B) a biosynthesis amount of 1-octen-3-ol according to reaction temperature and reaction time in a transformant yeast.

MODES OF THE INVENTION

Hereinafter, the present application will be described in more detail with reference to Examples according to the present application. However, the following Examples of the present application are only an example of the present application. These Examples are intended to describe the present application in more detail, and it will be apparent to those skilled in the art that the scope of the present application as set forth in the appended claims is not limited by these Examples.

Example 1: Isolation of Total RNA from Pine Mushroom

Figure 1:
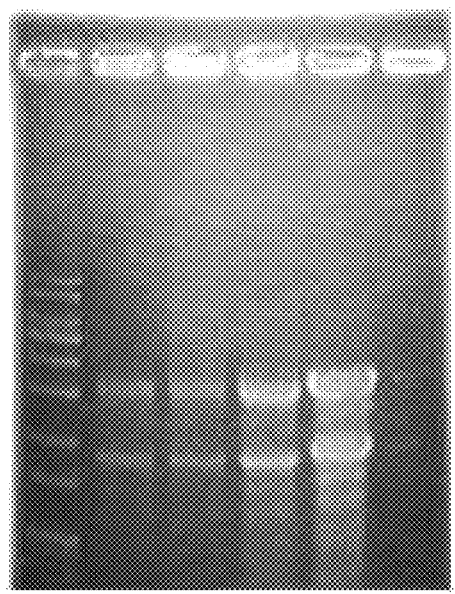
FIG. 1 is an electrophoretic photograph showing total RNA extracted from pine mushroom of the present application.

Total RNA was isolated from pine mushroom fruiting bodies collected in the Gachang area near Daegu. After the fruiting bodies were cut into small pieces of 3 to 5 cm, the cut fruiting bodies were finely ground with a mortar using liquid nitrogen. The ground fruiting bodies were completely dissolved in 1 mL of TRIZol, added with chloroform, and centrifuged for 15 minutes to isolate RNA. A supernatant containing RNA was transferred to a new tube, add with the same amount of iso-propyl alcohol, reacted at room temperature for 15 minutes, and centrifuged at 12,000 rpm for 10 minutes to precipitate RNA. Next, the supernatant was removed, washed by adding 75% ethyl alcohol, and then added with diethypyrocarbonate (DEPC)-treated water to elute and isolate total RNA. As a result, it was confirmed that the total RNA concentration was 992.8 ng/μl (A260/A280=1.886) (in FIG. 1, Line 1 indicated a DNA marker, and Lanes 2 to 4 indicated Total RNA).

Example 2: cDNA Synthesis of Pine Mushroom

First strand cDNA was synthesized by the following method using the total RNA obtained in Example 1 and an Accuscript High Fidelity 1st Strand cDNA Synthesis kit (Stratagene). 1 μl of Total RNA, 11.7 μl of RNase-free water, 2 μl of an AccuScript RT buffer, 1 μl of an Oligo dT primer, and 0.8 μl of a dNTP mixture were mixed and reacted at 65° C. for 5 minutes and at room temperature for 5 minutes, then further added with DTT 100 mM, 1 μl of AccuScript RT, and 0.5 μl of RNase Block ribonuclease, reacted at 42° C. for 1 hour, and then reacted at 70° C. for 15 minutes to synthesize cDNA.

Example 3: Preparation of PCR Products of Lipoxygenase-1, 2, 3 Genes and Hydroperoxide Lyase Gene Genes were amplified using PrimeSTAR™ HS Polymerase (TaKaRa) with the cDNA synthesized and obtained in Example 2 as a template, the following primers (Table 1), and PCR conditions (Table 2). PCR was performed using the corresponding genes and restriction enzymes in a SC selectable medium.

TABLE 1

| Name | Sequences (5'-3') | Restriction enzyme |
| --- | --- | --- |
| LOX1-F-HindIII (SEQ ID NO: 1) | AAGCTTAACACAATGTCCTTAAGCAAGTTTCCG | HindIII |
| LOX1-R-KpnI (SEQ ID NO: 2) | GGTACCACCTTCGTTACATCATACTGTAT | KpnI |
| LOX2-F-KpnI (SEQ ID NO: 3) | GGTACCAACACAATGTTGACGCGGTTATTTAAG | KpnI |
| LOX2-R-NotI (SEQ ID NO: 4) | GCGGCCGCATATCGAACTGCACAACGAGGG | NotI |
| LOX3-F-HindIII (SEQ ID NO: 5) | AAGCTTAACACAATGTCGATTGATTCTGTTCCA | HindIII |
| LOX3-R-KpnI (SEQ ID NO: 6) | GGTACCATGGCACAGTACTCCCGTTGCCA | KpnI |
| HPL-F-KpnI (SEQ ID NO: 7) | GGTACCAACACAATGTCCCTCAAGCATTCTTCC | KpnI |
| HPL-R-EcoRI (SEQ ID NO: 8) | GAATTCTGGATGTTGTGTCCGTGGCGATA | EcoRI |

TABLE 2

| Target gene | Pre-denaturation | Denaturation | Anealing | Extension |
| --- | --- | --- | --- | --- |
| Lipoxygenase-1 (SEQ ID NO: 9) | 98° C., 3 min | 98° C., 10 sec | 60° C., 15 sec | 72° C., 3 min |
| Lipoxygenase-2 (SEQ ID NO: 10) | 98° C., 3 min | 98° C., 10 sec | 58° C., 15 sec | 72° C., 4 min |
| Lipoxygenase-3 (SEQ ID NO: 11) | 98° C., 3 min | 98° C., 10 sec | 56° C., 15 sec | 72° C., 4 min |
| Hydroperoxidelyase (SEQ ID NO: 12) | 98° C., 3 min | 98° C., 10 sec | 59° C., 5 sec | 72° C., 2 min |

Figure 2:
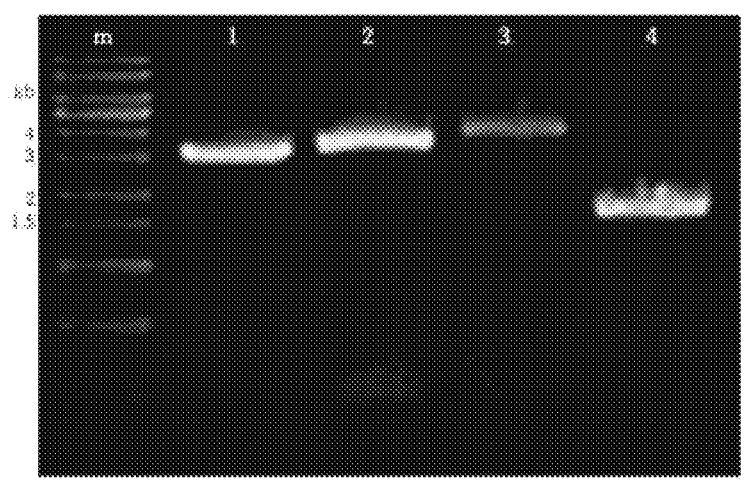
FIG. 2 is an electrophoretic photograph showing amplification of a lipoxygenase-1 gene, a lipoxygenase-2 gene, and a lipoxygenase-3 gene (Lanes 1, 2, and 3, respectively), and a hydroperoxide lyase gene (Lane 4) of the present application.

As a result of the experiment, through an electrophoretic photograph, it was confirmed that a lipoxygenase-1 gene (SEQ ID NO: 9, 3159 bp), a lipoxygenase-2 gene (SEQ ID NO: 10, 3333 bp), and a lipoxygenase-3 gene (SEQ ID NO: 11, 3855 bp) (Lanes 1, 2, 3 in FIG. 2, respectively), and a hydroperoxide lyase gene (SEQ ID NO: 12, 1,560 bp, Lane 4 in FIG. 2) were amplified. In Lane 1 of the electrophoretic photograph of FIG. 2, a Plus DNA Ladder marker was used as a DNA marker.

Example 4: Gene Cloning Using pGEM™ Easy T Vector

In order to clone PCR products of a lipoxygenase-1 gene, a lipoxygenase-2 gene, a lipoxygenase-3 gene, and a hydroperoxide lyase gene obtained in Example 3 with each pGEM™ easy T vector (Promega), a A-tailing process was performed using a Mighty TA-cloning Reagent Set (TaKaRa), ligation with the pGEM™ easy T vector was performed overnight at 4° C., and then the ligated vector was transformed into E. coli DH5a competent cells (TaKaRa). Next, E. coli was smeared on a Luria Broth (LB) medium plate added with ampicillin (100 μl/ml), IPTG (0.1 mM), and X-gal (50 μg/ml), and incubated at 37° C. for 16 to 18 hours, and thereafter, a plasmid was extracted using a Higene™ Plasmid Mini Prep kit (Biofact). To confirm whether the gene was correctly inserted into the extracted plasmid, the size of the gene was checked by electrophoresis, and then sequencing of the corresponding base sequence was performed.

Figure 3:
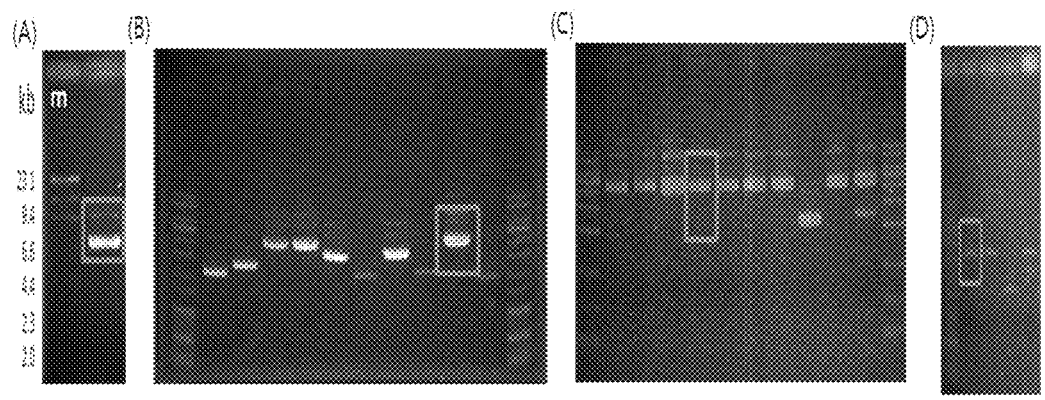
FIG. 3 is an electrophoretic photograph showing results of inserting a lipoxygenase-1 gene (A), a lipoxygenase-2 gene (B), a lipoxygenase-3 gene (C), and a hydroperoxide lyase gene (D) of the present application into a pGEM™ easy T vector plasmid.

As a result of the experiment, It was confirmed that s lipoxygenase-1 gene (FIG. 3(A)), a lipoxygenase-2 gene (FIG. 3(B)), a lipoxygenase-3 gene (FIG. 3(C)) and a hydroperoxide lyase gene (FIG. 3(D)) were accurately inserted into the pGEM™ easy T vector plasmid.

Example 5: Gene Cloning Using Yeast Expression Vector

Figure 4:
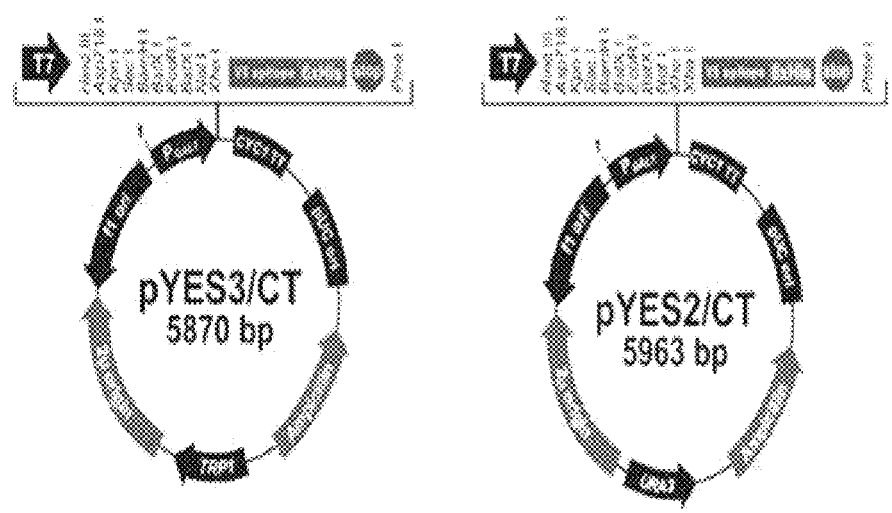
FIG. 4 is a schematic diagram showing a map of pYES3/CT and pYES2/CT yeast expression vectors.
Figure 5:
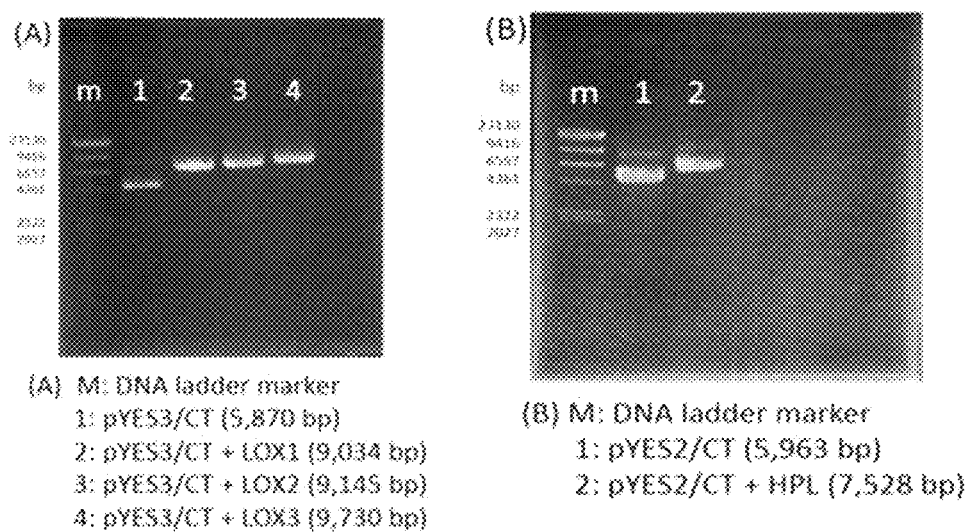
FIG. 5 is an electrophoretic photograph showing results of inserting a lipoxygenase-1 gene, a lipoxygenase-2 gene, and a lipoxygenase-3 gene (A), and a hydroperoxide lyase gene (B) into a plasmid.

The pGEM vectors inserted with the lipoxygenase-1 gene, the lipoxygenase-2 gene, and the lipoxygenase-3 gene for gene expression in the yeast reacted at 37° C. and were cleaved with restrictions enzymes HindIII and KpnI, and the pGEM vector inserted with the hydroperoxide lyase gene reacted at 37° C. and was cleaved with restrictions enzymes KpnI and EcoRI. The cleaved genes were quantified after purification with a TaKaRa MiniBEST Agarose Gel DNA Extraction kit (TaKaRa). After selecting Saccharomyces cerevisiae species as a microbial model for expressing the genes, a pYES3 vector (Invitrogen Co., Ltd.), which was a yeast expression vector suitable for a host cell, was selected for efficient protein expression. This vector includes a pUc ori sequence to be easily amplified in bacteria, and includes a 2μ origin sequence to be amplified even in yeasts. In addition, this vector had a multiple cloning site as a restriction enzyme site that did not cleave a target gene to accurately insert the gene into the vector. The vector has a GAL1 promoter which a strong promoter, a T7 promoter, and a CYC1 sequence to accurately determine the insertion of the gene and the inserted sequence by gene sequencing analysis. In addition, since a TRP1 gene sequence, which is a selectable marker, is present to easily screen the yeasts inserted with the vector, and a V5 epitope and a 6×His tag sequence are present to make it easy to detect the expressed target protein. In order to transform two different types of genes into the yeast together, a pYES2 vector with a different selectable marker URA3 from a pYES3 vector was selected. The pYES2 vector has the same other characteristics as the pYES3 vector and is larger in size by about 100 bp (FIG. 4). Since the yeast into which all of the genes have been inserted may be efficiently screened using the selectable marker, cloning was performed using the following method. The lipoxygenase-1 gene, the lipoxygenase-2 gene, and the lipoxygenase-3 gene were subjected to overnight ligation reaction with a pYES3/CT vector (Invitrogen), and the hydroperoxide lyase gene was subjected to overnight ligation reaction with a pYES2/CT vector (Invitrogen) at 4° C. to be transformed into *E. coli* DH5a competent cells (TaKaRa). The transformed cells were smeared on a Luria Broth (LB) medium plate added with ampicillin (100 µl/ml), IPTG (0.1 mM), and X-gal (50 µg/ml) and incubated at 37° C. for 16 to 18 hours. Next, the plasmid was extracted from the screened *E. coli* using a Higene™ Plasmid Mini Prep kit (Biofact), and the size of the extracted plasmid was checked by electrophoresis to confirm whether each gene was correctly inserted, and then base sequence sequencing was performed. As a result of the experiment, it was confirmed that the lipoxygenase-1 gene, the lipoxygenase-2 gene, the lipoxygenase-3 gene, and the hydroperoxide lyase gene were correctly inserted into the plasmid (FIG. 5). That is, the lanes of FIG. 5(A) illustrate electrophoretic results of m: DNA ladder marker, 1: pYES3/CT, 2: pYES3/CT+Lipoxygenase-1 gene, 3: pYES3/CT+Lipoxygenase-2 gene, and 4: pYES3/CT+Lipoxygenase-3 gene, and the lanes of FIG. 5(B) illustrate electrophoretic results of m: DNA ladder marker, 1: pYES2/CT, and 2: pYES2/CT+Hydroperoxide lyase.

Example 6: Transformation of Yeast Expression Vectors into INVSc1 Yeast

*Saccharomyces cerevisiae* competent cells were prepared using a S.C. EasyComp™ Transformation kit (Invitrogen). In addition, the pYES3/CT vectors introduced with the lipoxygenase-1 gene, the lipoxygenase-2 gene, and the lipoxygenase-3 gene obtained in Example 5, and the pYES2/CT vector introduced with the hydroperoxide lyase were mixed in a ratio of 1:1, respectively. Thereafter, these vectors were transformed into *S. cerevisiae* competent cells (INVSc1). In addition, the *S. cerevisiae* competent cells (INVSc1) were smeared on an SC medium plate (Synthetic complete medium, 0.67% yeast nitrogen base, 2% glucose, 0.192% yeast synthetic drop-out medium supplements, 2% agar) in which tryptophan and uracil were deleted and then incubated at 30° C. for 2 to 3 days (FIG. 6(A)). The SC medium was a minimal medium in which tryptophan and uracil were deleted, and was used because the SC medium efficiently selected a transformant yeast into which both a pYES3 vector with a TRP1 gene and a pYES2 vector with a URA3 gene were inserted and was suitable for expression of a target protein. The composition of the SC medium used was shown in Table 3 below.

TABLE 3

| Composition ratio (%, W/W) | Composition contents |
|---|---|
| 0.67% | Yeast nitrogen base (without amino acids) |
| 2% | Carbon source (adding raffinose for screening and incubation of transformant and galactose for protein expression) |
| 0.01% | Adenine, arginine, cysteine, leucine, lysine, threonine |
| 0.005% | Aspartic acid, histidine, isoleucine, methionine, phenylalanine, proline, serine, tyrosine, valine |
| 2% | Agar (for solid medium) |
| Total 100% | Constituted 100% with H$_2$O. |

Next, as a result of screening transformed yeasts into which two types of genes were introduced by performing colony PCR, it was confirmed that the lipoxygenase-1 gene, the lipoxygenase-2 gene, the lipoxygenase-3 gene, and the hydroperoxide lyase gene were transformed into INVSc1 through yeast expression vectors (FIG. 6(B)). Yeasts KMG 1801, KMG 1802, and KMG 1803 transformed in a 1:1 ratio of the lipoxygenase-1 gene, the lipoxygenase-2 gene, the lipoxygenase-3 gene, and the hydroperoxide lyase gene were deposited with deposit numbers KCTC13476BP, KCTC13477BP, and KCTC13478BP in the Korean Collection for Type Cultures (KCTC) on Feb. 6, 2018. In addition, in order to confirm the growth of the yeast transformed with each combination of the lipoxygenase-1 gene, the lipoxygenase-2 gene, the lipoxygenase-3 gene, and the hydroperoxide lyase gene, 5 mL of each incubation medium was incubated and then used as a sample for measuring a growth curve of the yeast every 0, 4, 8, 12, 16, 20, 24, 28, 32, and 36 hours. As a result of the measurement, it was confirmed that KMG 1801 (Deposit No. KCTC13476BP, FIG. 7(A)) and KMG 1802 (Deposit No. KCTC 13477BP, FIG. 7(B)) grew rapidly in a period of 8 to 12 hours, and KMG 1803 (Deposit No. KCTC13478BP, FIG. 7 (C)) grew rapidly in a period of 28 to 32 hours.

Example 7: Identification of 1-octen-3-ol Biosynthesis in Transformed Yeasts Introduced with Lipoxygenase and Hydroperoxide Lyase Genes In order to confirm the biosynthesis of 1-octen-3-ol in yeasts transformed with the combinations of each gene obtained from Example 6, the transformed yeasts were inoculated in a SC selectable medium (Synthetic complete medium, 0.67% yeast nitrogen base, 2% raffinose, 0.192% yeast synthetic drop-out medium supplements) in which tryptophan and uracil were deleted, pre-incubated overnight, and then centrifuged to collect yeasts. The collected yeasts were inoculated in a SC induction medium (Synthetic complete medium, 0.67% yeast nitrogen base, 1% raffinose, 2% galactose, 0.192% yeast synthetic drop-out medium supplements) in which tryptophan and uracil were deleted, added with 2% Tween-20 and 1.5 mM linoleic acid, and then incubated at 30° C. for 20 hours. The incubated yeasts and the media were isolated by centrifugation, and the yeasts were added with a sodium phosphate lysis buffer (50 mM sodium phosphate, 1 mM PMSF, 5% glycerol, 2% triton X-100; pH 6.5) and acid-washed glass beads (0.4 to 0.6 mm size), lyzed with a bead beater, and then the cells were down by centrifugation and a cell lysis supernatant was recovered. Next, in order to confirm the produced 1-octen-3-ol, lysates and the incubated medium were analyzed by gas chromatography-mass spectrometry (Aqilent 7890B GC & 5977B MSD) by extracting volatile components through solid phase microextraction (SPME) for 35 minutes at 70° C. For the gas chromatography-mass spectrometry, DB-WAX (60 m×250 μm×0.25 μm) and helium carrier gas were used, and the temperature of the column was increased from 40° C. to 120° C. at a rate of 2° C./min and increased from 120° C. to 240° C. at a rate of 20° C./min. The temperature of the injector was set to 250° C.

As a result of the experiment, as illustrated in FIG. 8, peaks were not observed in (A) lysates of cells incubated without adding a substrate and (B) a medium incubated without adding a substrate, but peaks of 1-octen-3-ol at 38.27 min were checked in (C) lysates of cells incubated by adding a substrate and (D) a medium incubated by adding a substrate.

Meanwhile, the results for 1-octen-3-ol biosynthesis according to the combination of each lipoxygenase gene and hydroperoxide lyase were shown in Table 4. According to Table 4, it was confirmed that there was a biosynthetic effect of 1-octen-3-ol in all yeasts into which each combination of the genes Lipoxygenase-1, Lipoxygenase-2, Lipoxygenase-3, and Hydroperoxide lyase found in the fruiting bodies of pine mushroom was introduced, and the degree of biosynthesis was varied according to a type of combination. In addition, it was confirmed that the 1-octen-3-ol biosynthesis concentration was highest when the lipoxygenase-1 was used.

TABLE 4

| | Protein combination | Retention time (min) | Concentration (mg/L) |
|---|---|---|---|
| 1 | Lipoxygenase-1 + Hydroperoxide lyase | 38.270 | 0.66 |
| 2 | Lipoxygenase-2 + Hydroperoxide lyase | 38.269 | 0.33 |
| 3 | Lipoxygenase-3 + Hydroperoxide lyase | 38.270 | 0.58 |
| 4 | Lipoxygenase-1 + 2 + Hydroperoxide lyase | 38.271 | 0.42 |
| 5 | Lipoxygenase-1 + 3 + Hydroperoxide lyase | 38.271 | 0.38 |
| 6 | Lipoxygenase-2 + 3 + Hydroperoxide lyase | 38.270 | 0.27 |
| 7 | Lipoxygenase-1 + 2 + 3 + Hydroperoxide lyase | 38.267 | 0.56 |

Experimental Example 1: Optimization of 1-octen-3-ol Biosynthesis According to Substrate Concentration and Reaction Conditions In order to confirm the biosynthesis amount of 1-octen-3-ol in transformed yeasts according to the concentration of a substrate and reaction conditions, the yeasts transformed with lipoxygenase-1 and hydroperoxide lyase were inoculated in a SC selectable medium (Synthetic complete medium, 0.67% yeast nitrogen base, 2% raffinose, 0.192% yeast synthetic drop-out medium supplements) in which tryptophan and uracil were deleted, pre-incubated overnight, and then centrifuged to collect yeasts. The collected yeasts were inoculated in a SC induction medium (Synthetic complete medium, 0.67% yeast nitrogen base, 1% raffinose, 2% galactose, 0.192% yeast synthetic drop-out medium supplements) in which tryptophan and uracil were deleted, added with 2% Tween-20 and an appropriate concentration (0 to 0.1 M) of linoleic acid, and then incubated at 30° C. for 20 hours. In addition, in order to confirm the biosynthesis amount of 1-octen-3-ol in the transformed yeasts according to reaction conditions, the pre-incubated yeasts were inoculated in a SC induction medium (Synthetic complete medium, 0.67% yeast nitrogen base, 1% raffinose, 2% galactose, 0.192% yeast synthetic drop-out medium supplements) in which tryptophan and uracil were deleted, added with 2% Tween-20 and 3 mM linoleic acid, and then incubated at 15° C. and 30° C. for 12, 24, 36, and 48 hours, respectively. The incubated yeasts were collected by centrifugation, added with a sodium phosphate lysis buffer (50 mM sodium phosphate, 1 mM PMSF, 5% glycerol, 2% triton X-100; pH 6.5) and acid-washed glass beads (0.4 to 0.6 mm size), and lyzed with a bead beater. Thereafter, the cells were down by centrifugation, a cell lysis supernatant was recovered, and added with 0.1 g of NaCl (for protein precipitation), and then fragrances were extracted with the same amount of diethyl ether and analyzed by gas chromatography-mass spectrometry (Aqilent 7890B GC & 5977B MSD). For the gas chromatography-mass spectrometry, DB-WAX (60 m×250 μm×0.25 μm) and helium carrier gas were used, and the temperature of the column was increased from 40° C. to 120° C. at a rate of 2° C./min and increased from 120° C. to 240° C. at a rate of 20° C./min. The temperature of the injector was set to 250° C. The concentration of the biosynthesized 1-octen-3-ol was compared with a 1-octen-3-ol standard (Sigma) and analyzed. As a result of the experiment, the biosynthesis amount of 1-octen-3-ol was highest at about 0.48 mg/L when the added concentration of linoleic acid was 3 mM (A), and the biosynthesis amount of 1-octen-3-ol was highest at about 0.35 mg/L at 30° C. for 24 hours (B) (FIG. 9).

INDUSTRIAL APPLICABILITY

The present application relates to a transformed yeast producing 1-octen-3-ol and a method for producing the same, which is a useful invention in the cosmetic industry and food development industry using a pine mushroom flavor.

Depositary Authority Name: Korean Collection for Type Cultures (KCTC)
Accession number: KCTC13476BP
Accession Date: 20180206
Depositary Authority Name: Korean Collection for Type Cultures (KCTC)
Accession number: KCTC13477BP
Accession Date: 20180206
Depositary Authority Name: Korean Collection for Type Cultures (KCTC)
Accession number: KCTC13478BP
Accession Date: 20180206

Budapest Treaty on the International Recognition of the Deposit of Microorganisms for the Purpose of Patent Procedure International Form Receipt in the Case of an Original Deposit Issued Pursuant to Rule 7.1

TO: Kyungpook National University Industry-Academic Cooperation/Gyeongsangbuk-do Forest Environment Research Institute
80, Daehak-ro, Buk-gu, Daegu, Republic of Korea/36780, Tongil-ro, Gyeongju-si, Gyeongsangbuk-do, Republic of Korea

| | |
|---|---|
| I. IDENTIFICAION OF THE MICROORGANISM | |
| Identification reference given by the DEPOSITOR (Microorganism name): *Saccharomyces cerevisiae* KAIG 1801 | Accession number given by the INTERNATIONAL DEPOSITARY AUTHORITY: KCTC 13476BP |
| II. SCIENTIFIC DESCRIPTION AND/OR PROPOSED TAXONOMIC DESIGNATION The microorganism identified under I above was accompanied by: a scientific description a proposed taxonomic designation (Mark with a cross where applicable) | |
| III. RECEIPT AND ACCEPTANCE This International Depository Authority accepts the microorganism identified under I above, which was received by it on Feb. 6, 2018. | |
| IV. RECEIPT OF REQUEST FOR CONVERSION The microorganism identified under I above was received by this International Depository Authority under the Budapest Treaty. | |
| V. INTERNATIONAL DEPOSITARY AUTHORITY | |
| Authority Name: Korean Collection for Type Cultures (KCTC) Korea Research Institute of Bioscience and Biotechnology (KRIBB) Address: 181, Ipsin-gil, Jeongeup-si, Jeollabuk-do 56212, Republic of Korea | Signature(s) of person(s) having the power to represent the International Depository Authority of authorized official(s): Date: Feb. 6, 2018 Cha-Young, Kim |

Form BP/4 (KCTC Form 17)

No difference from the original Patent Attorney Duck-Rog, Lee

Budapest Treaty on the International Recognition of the Deposit of Microorganisms for the Purpose of Patent Procedure International Form Receipt in the Case of an Original Deposit Issued Pursuant to Rule 7.1

TO: Kyungpook National University Industry-Academic Cooperation/Gyeongsangbuk-do Forest Environment Research Institute
80, Daehak-ro, Buk-gu, Daegu, Republic of Korea/36780, Tongil-ro, Gyeongju-si, Gyeongsangbuk-do, Republic of Korea

| | |
|---|---|
| I. IDENTIFICAION OF THE MICROORGANISM | |
| Identification reference given by the DEPOSITOR (Microorganism name): *Saccharomyces cerevisiae* KAIG 1802 | Accession number given by the INTERNATIONAL DEPOSITARY AUTHORITY: KCTC 13477BP |
| II. SCIENTIFIC DESCRIPTION AND/OR PROPOSED TAXONOMIC DESIGNATION The microorganism identified under I above was accompanied by: a scientific description a proposed taxonomic designation (Mark with a cross where applicable) | |
| III. RECEIPT AND ACCEPTANCE This International Depository Authority accepts the microorganism identified under I above, which was received by it on Feb. 6, 2018. | |
| IV. RECEIPT OF REQUEST FOR CONVERSION The microorganism identified under I above was received by this International Depository Authority under the Budapest Treaty. | |
| V. INTERNATIONAL DEPOSITARY AUTHORITY | |
| Authority Name: Korean Collection for Type Cultures (KCTC) Korea Research Institute of Bioscience and Biotechnology (KRIBB) Address: 181, Ipsin-gil, Jeongeup-si, Jeollabuk-do 56212, Republic of Korea | Signature(s) of person(s) having the power to represent the International Depository Authority of authorized official(s): Date: Feb. 6, 2018 Cha-Young, Kim |

Form BP/4 (KCTC Form 17)

No difference from the original Patent Attorney Duck-Rog, Lee

Budapest Treaty on the International Recognition of the Deposit of Microorganisms for the Purpose of Patent Procedure International Form Receipt in the Case of an Original Deposit Issued Pursuant to Rule 7.1

TO: Kyungpook National University Industry-Academic Cooperation/Gyeongsangbuk-do Forest Environment Research Institute
80, Daehak-ro, Buk-gu, Daegu, Republic of Korea/36780, Tongil-ro, Gyeongju-si, Gyeongsangbuk-do, Republic of Korea I. IDENTIFICAION OF THE MICROORGANISM
Identification reference given by the DEPOSITOR (Microorganism name): *Saccharomyces cerevisiae* KAIG 1803

Accession number given by the INTERNATIONAL DEPOSITARY AUTHORITY: KCTC 13478BP

II. SCIENTIFIC DESCRIPTION AND/OR PROPOSED TAXONOMIC DESIGNATION
The microorganism identified under I above was accompanied by:
a scientific description
a proposed taxonomic designation
(Mark with a cross where applicable)

III. RECEIPT AND ACCEPTANCE
This International Depository Authority accepts the microorganism identified under I above, which was received by it on Feb. 6, 2018.

IV. RECEIPT OF REQUEST FOR CONVERSION
The microorganism identified under I above was received by this International Depository Authority under the Budapest Treaty.

V. INTERNATIONAL DEPOSITARY AUTHORITY
Authority Name: Korean Collection for Type Cultures (KCTC) Korea Research Institute of Bioscience and Biotechnology (KRIBB)
Address: 181, Ipsin-gil, Jeongeup-si, Jeollabuk-do 56212, Republic of Korea Signature(s) of person(s) having the power to represent the International Depository Authority of authorized official(s):
Date: Feb. 6, 2018
Cha-Young, Kim Form BP/4 (KCTC Form 17)

No difference from the original Patent Attorney Duck-Rog, Lee

The invention claimed is:

1. A transformed yeast for producing 1-octen-3-ol transformed with a recombinant vector comprising the nucleotide sequence of any of SEQ ID NOs: 9, 10 and 11 encoding lipoxygenase and the nucleotide sequence of SEQ ID NO: 12 encoding hydroperoxide lyase.

2. A method for producing a transformed yeast for producing 1-octen-3-ol comprising the steps of:
  isolating total RNA of pine mushroom and synthesizing cDNA;
  PCR-amplifying a lipoxygenase gene comprising the nucleotide sequence of any of SEQ ID NOs: 9-11 and a hydroperoxide lyase gene comprising the nucleotide sequence of SEQ ID NO: 12 from the synthesized cDNA;
  gene-cloning each of the amplified lipoxygenase gene and hydroperoxide lyase gene in a vector;
  gene-cloning each of the cloned lipoxygenase gene and hydroperoxide lyase gene in each yeast expression vector; and
  transforming and incubating the yeast expression vector into a yeast to produce 1-octen-3-ol.

3. The method of claim 2, wherein the yeast expression vector is a vector selected from a pYES3/CT vector and a pYES2/CT vector.

4. The method of claim 3, wherein the pYES3/CT vector and the pYES2/CT vector are used in a ratio of 1:1.

5. The method of claim 2, wherein the yeast is incubated in a SC medium using 0.01 to 100 mM of linoleic acid at 15° C. to 45° C. for 12 to 48 hours.

6. The method of claim 2, wherein the yeast is *Saccharomyces cerevisiae*.

7. A method for producing 1-octen-3-ol comprising the steps of:
  biosynthesizing 1-octen-3-ol by incubating the transformed yeast for producing the 1-octen-3-ol of claim 1 in a medium; and
  obtaining the biosynthesized 1-octen-3-ol.

* * * * *

SEQUENCE LISTING

<160> NUMBER OF SEQ ID NOS: 12

<210> SEQ ID NO 1
<211> LENGTH: 33
<212> TYPE: DNA
<213> ORGANISM: Artificial Sequence
<220> FEATURE:
<223> OTHER INFORMATION: Synthetic: LOX1-F-HindIII

<400> SEQUENCE: 1
aagcttaaca caatgtcctt aagcaagttt ccg        33

<210> SEQ ID NO 2
<211> LENGTH: 29
<212> TYPE: DNA
<213> ORGANISM: Artificial Sequence
<220> FEATURE:
<223> OTHER INFORMATION: Synthetic: LOX1-R-KpnI

<400> SEQUENCE: 2
ggtaccacct tcgttacatc atactgtat        29

<210> SEQ ID NO 3
<211> LENGTH: 33

```
-continued

<212> TYPE: DNA
<213> ORGANISM: Artificial Sequence
<220> FEATURE:
<223> OTHER INFORMATION: Synthetic: LOX2-F-KpnI

<400> SEQUENCE: 3
ggtaccaaca caatgttgac gcggttattt aag                            33

<210> SEQ ID NO 4
<211> LENGTH: 30
<212> TYPE: DNA
<213> ORGANISM: Artificial Sequence
<220> FEATURE:
<223> OTHER INFORMATION: Synthetic: LOX2-R-NotI

<400> SEQUENCE: 4
gcggccgcat atcgaactgc acaacgaggg                                30

<210> SEQ ID NO 5
<211> LENGTH: 33
<212> TYPE: DNA
<213> ORGANISM: Artificial Sequence
<220> FEATURE:
<223> OTHER INFORMATION: Synthetic: LOX3-F-HindIII

<400> SEQUENCE: 5
aagcttaaca caatgtcgat tgattctgtt cca                            33

<210> SEQ ID NO 6
<211> LENGTH: 29
<212> TYPE: DNA
<213> ORGANISM: Artificial Sequence
<220> FEATURE:
<223> OTHER INFORMATION: Synthetic: LOX3-R-KpnI

<400> SEQUENCE: 6
ggtaccatgg cacagtactc ccgttgcca                                 29

<210> SEQ ID NO 7
<211> LENGTH: 33
<212> TYPE: DNA
<213> ORGANISM: Artificial Sequence
<220> FEATURE:
<223> OTHER INFORMATION: Synthetic: HPL-F-KpnI

<400> SEQUENCE: 7
ggtaccaaca caatgtccct caagcattct tcc                            33

<210> SEQ ID NO 8
<211> LENGTH: 29
<212> TYPE: DNA
<213> ORGANISM: Artificial Sequence
<220> FEATURE:
<223> OTHER INFORMATION: Synthetic: HPL-R-EcoRI

<400> SEQUENCE: 8
gaattctgga tgttgtgtcc gtggcgata                                 29

<210> SEQ ID NO 9
<211> LENGTH: 3158
<212> TYPE: DNA
<213> ORGANISM: Artificial Sequence
<220> FEATURE:
<223> OTHER INFORMATION: Synthetic: lipoxygenase-1

<400> SEQUENCE: 9
```

-continued

```
atgtccttaa gcaagtttcc gtccatcttt cgcaaatcca ccctgcccaa cggcacggtg      60
aatggtgatg cgacggccac atccacccaa gccatcaggg acgtccatgt taagaaaggt    120
tccccattta ctcaaatttt ggacccatct accatctcgt ctgtcgtgga tgccttcagg    180
cataaggagt ctctcgacga caggaaattc gctcttgagc atgctcttac cttcatttcc    240
cgcacggatg aaggtccact tcaaacagag ctacagaaca aaattgttga gctcttatac    300
aatgatttgg gtcacccgcc cgcgacgagc attggcaacc actacgcgtg gcgaacggct    360
gatggatctt ttaataacat cgatctcccg gaaataggca aggctggcac cccatatgct    420
cgctcagttc aacaatcgca tccccttccg aagaaccaat tgcctgatcc tggactcatc    480
ttcgatactc ttttgaagcg ggaaggtttc gaggaacatc ctgctgggct atcttctttg    540
atgtttccct tgccgctttt agttatccac actgttttcc gtacatcaca cagaaatgtg    600
gacatcaatg aaacctcatc ctacgttgac ctttcgccgt tgtatggaca taaccaagag    660
gcacaggaca aagtccgcgt tcgagacggt cgaggcttgc ttctcccaga cgttttttgct   720
gaggataggt tacttcttct cccgcctgcc gtttgtgcgc tcctcgtctt gttcagtcgc    780
aaccataact acattgcaaa gaaactcttg gatataaatg agagaggcac ttacgttgac    840
ccgtccacgc tgcgctcgga taaaccagcc gaaaaagcca agctcctggc acaggaagag    900
gaactcttcc agatcgctcg tttaattaac tgtggctggt ttgcttctgt cgtgttttcg    960
gactacttct cgtgtatctt aggtctggtt agaactggaa gcagttggag cttggacccg   1020
ttccaggaaa tcaggaatca ggatcactct gttttcgagc gaggtaaagg gaatgcctgc   1080
agtgttgagt tcaactgcct gtatcgatgg cacgctacca ctagcgtaaa ggacgaagaa   1140
tgggtcgccc aagtttttga aaggtcttc gatggtaaag atccggaagc agtcactcct   1200
gaggacttta aggctgctgg gcataggata gccgctacgc agcctgacat cacccattgg   1260
actttcgggg atttgcaacg ccaggcggat ggcactttca aggatgaaga tttggccagt   1320
cttatacaca atgcaacgga acatccggct ggagctttcc gtgcccgagg aacaccagct   1380
gtcatgcgcc ttcatgaaat aatggggatc gagcagaaca aagatgggg agtctgctcg    1440
ctaaatgatt ttaggaagtt ccttggcttg aggccataca agtccttcaa ggagtggaac   1500
ccgaggcccg atattgctga agctgccgag aagctatatg gtgacatcga ccatctcgag   1560
ctatatgtcg gccttcaagc agaagatgcc aagcctgtca tggatggagc aggactttgt   1620
cctggatata caatcagccg agctattctt agcgacgcaa ttgctctcac tcgagggga   1680
agattcttca ctcaagatta ttccccacac aatctgactg cttggggatt tgctgattgc   1740
cagagggatc ctaatgcgtt cggattcggc agcactcttg gccggctctt tttacgcaat   1800
cttcccaaca atttcacaga aaatagcgta tacacttttct tccctttgat gactcccgac   1860
gccatgaaga cccatttgtc gaagctgaag ctgatcgatc agtatgattt cacacgtccc   1920
aaagatcaat cgggcgtgaa ggaggtcaat gattatgcgc aagtgactga gatacttagc   1980
aatcctgctg cctttgtatc atcttatgcc gaacaagctg ccagagttat caacggcaaa   2040
gggttttaca cggctcagca agacacggaa gaaaacaaaa ttgccaaagc attggcggac   2100
tcgccagagg ctcttgacaa gatcgggaaa tacttctatg atactacttc tcacttgatc   2160
aagtcaaatt cgttctcgct cgtcggtgat aaagtacgtg gtgttgacat agtgcgagat   2220
gtcttcaggg ttgttcctat attgtgggct gcagcggaca tcggtggcat cgagttgaag   2280
acaaaggacc atcctgatgg cgcatacacc ccttcagagc tgtacgatat tctgggtgat   2340
atctatacat tcgtcttcct tgagattgaa cctgctaatg tcatggtgct tggtgccaaa   2400
```

```
gtccgtcacg atactcgcga attgttgggc catatcaaga accatttgta tggtgcgggt    2460
ggtgtacgcg gttctttcac cggcttcgtt agctcgctct tcaccaggtc caggaaaccc    2520
gaacaccacg aacttgtcaa gcgtctttcc caacttgggc aatcgtcgga cgacctcgct    2580
acaaatattt tggctctttt ggtctcggcg acagttgaat tgtcccttgc tttgactaat    2640
atgataaatc tctatcttgg tagggaggag ggaactaaga tctcttcgtt gataaagagt    2700
gccgatggca atgccttgct tgatggttat gcgcgcgagg ctttgagact tgacccacca    2760
ttccagggtg tatatcgggt tgcgacgaag gatcaagaag tcggaggtgt tgctgtcaag    2820
aaaaatgacc gggtgttcct agacatcgct tccgccaacg tcaacgaatc agtcttcgag    2880
tcagcccact ctgtcaatcc ttctcgaggc accaaaggct atctttcggt tgatggactc    2940
tttgtccact taggagaaat gacgactaag attatgacgg aggtccttcg agccgtctat    3000
ggatttgaaa atgttcgtcg ggcgcccagg atttctgggg aactcaaaag gttcaaggac    3060
cattctcgac cacagctccg ctatgcgtat ttggatcaac accaacgtac ctctgcatgg    3120
cctacttcat tgactataca gtatgatgta acgaagat                            3158
```

<210> SEQ ID NO 10
<211> LENGTH: 3334
<212> TYPE: DNA
<213> ORGANISM: Artificial Sequence
<220> FEATURE:
<223> OTHER INFORMATION: Synthetic: lipoxygenase-2

<400> SEQUENCE: 10

```
atgttgacgc ggttatttaa gaaactcttt atttccccac tccttcatat catcctcttc      60
ttttctaccc cactctttag gttcatatct gtaatgaaca tccttaatca ctttacccag     120
gcagtcgact tcgttacaga atcacacgca ccattggaca ccgacgctgc gtgtcctgaa     180
tcagatgaat cattcaagaa agtttcagag acgcttgaat tatggtctca tcccgctgtc     240
aaaatctccg atctccctgc attttgggat gcggtgaagc acgggaatac cattggtctc     300
gatgatcgca agctgttgct ggagaaggtc ctcgtcctga tggcccgata taagaactct     360
gatcgctcca tgcaaattca gcgttatgtg atagatcttc tgtacaaaga cttgcctcat     420 ccccccccgca gttatctgtg tcccccccaca ggcggctctg cagtggtaac taattcactc     480
ggcaacataa aatacgcgtt tcgtaccgcc gacgggtcca attacaatcc cttattcccc     540
tctcttggca agctgggtc tccatatgca cgctcagtcc ctggactccg tttcgtacca     600
aaacacgtac ttccagatcc tggtctcgtg ttcgacacgc tacttagacg agaggaattt     660
gttcctcatc ctggtgggat ctccagccta ttcttcgcat tcgcggactt ggtcatccat     720 agtatttca acacaaatca cacgattgg acaaagaacg atactagtag ctatctagat     780
ttaagtatcc tctacggaaa ctctgaaagt caggtgaatc aagtcagacg caaggacggg     840
acgggcaggc tttgggagga cgtattcgct gacagcagac tacttttcat gcctcctgct     900
agttgtgcac tattggtatt gttgagtcga accataatt acatcgctca gaagcttttg     960
aacatcaatg agaatggtac attcgttttt cctgttccgc aagacgaaca agcgcggctc    1020
gcccaagatg atgagatctt caatcgcgca cgaatggtta attgcggatt tttcctccag    1080
atcatcttag gagattatgt gggtgcaatt ttgggcctta ttcgtgacag gtccgattgg    1140
cgtctcgacc ctctcatgtc tatgcgagag tcagaccacg aggtttctcc gcaaggcaag    1200
ggaaacgtag tatctgtgga attcaatctt ctttaccggt ggcattctac attatcagcg    1260
```

```
caagatgctg aatggacaac aaacacgttc tcgaagctgt ttgagggcag agactcgagc    1320
cagatcaccg tccaagattt caagctggct gctcataagt acctgattcc gcacacggac    1380
gttaggacat gggagttcaa cggtctgaaa cgagaacctg atggacgctt caaagatgat    1440
gacttggcga gaactatcca agacgccact gaacatcgcg ctggagcctt aaaagctaga    1500
ggaacacccg aagctcttcg tatcattgag atacttggaa ttgagcaagg cagagcctgg    1560
gggacatgtt cgctcaacga atttagaaaa ttttaggac tcaagcccta aaaacgttc     1620 aaggagtgga accccgacga aagatacat actgctgcag cagctctata aagatatc      1680 gagaatcttg aattacatgt cggccttcag gcagaagaaa caaaagtccc gggacctgga    1740
gcaggcttat gcccgggtta cactatctct agggccatct ggcagatgc tgtctctctg     1800 actcgggggg atccattctt taccactgaa tttactccgt tcaatttgac ctcgtgggg     1860 tacgaagact gtcaatacga tactaaggac ggttcctatg gtggaatcct cactaagcta    1920
ctcttccgaa cgttgcctga tcattaccg gctggatctg catatgctca cttcccttc     1980 cttgatccag tgtacatgag ggaaattctc accaaagatg tgaacctcgt caacaaatac    2040
acatggaccc gaccgcaact cccctctgtt accggcgtaa tcaacagttt taatggtgtc    2100
aagcaagtcc tgtccgaccc ttctttcgtg tctgcctaca cgaccgcat attcgacatc     2160 attacaactc ccccaacggc cgacaaggaa gaccataaat tgactatctt gcacaaaact    2220
cgcagcgact tcgttaaagg tcgcaaaaat gtcgagagcc tgcttccata ttcagagcct    2280
cctcatgaaa cttgggcagg atattttacg aaggaagtca agctctgat tacagagaaa    2340 gcagtccacc atgttggaga taattcaaaa tacgttgaca tagttggaga cgtgatcaat    2400
ctggtgccag ttcgttgggt ttccgagaag attcttggac ttccgctcaa aactatctcc    2460
aacccctccg gtacttttta cgaacaagaa atgtataaga tgttcgcgaa tacggctcga    2520
tatgtcttct tgaacatcga tcccgcccat gattggcatt tacgggagag ctctgttgaa    2580
gcgtttagaa agatcttgaa cgtcacggag gctcatttag ctgggtgac accgacggaa    2640 attctcgacc atatagccat caaaaactat gatagtcacc ggttttgaa gcgagtccgc    2700 gaggctggaa cagattatac caccaaagag ttggccgcac aagtattttc cgccgtggtt    2760
cctactgccg ccctcttctc acaagtcatt gcgcatgtgg tcgatttcta ccttgacgac    2820
gacaagcgaa atgaacgaga ggagattgtc aagttggttt ccgcgtgtca tgacaaagaa    2880
acggtcgcga aaattatggt ttatgttcaa gaagctctac gccttaatcc aactgtctcg    2940
ggtgtatacc gcacggcggg caaagatgtt tccatcgaac attctagagt tcaagctggt    3000
cagagaatct ttgccagcat tgtcaatgcc aatgttgata cttacagatt tggagcaact    3060
cctaccacag caacctacga caagcctgat aatgcggctg gaatctttgg gtttggagag    3120
tatggacttc tctctgctca gttttttcgaa tccaccgctc cgactattct aggaacagtg    3180
cttggactga aaaatctcaa acgtgcccca ggacagtctg gaaaatttgc taggttcacg    3240
gaagaattgc atggtagccc gcagcagtgg tacatcaata tgcaagggaa gactacccct    3300
ttcccggatt ccctcgttgt gcagttcgat atgc                                3334
```

<210> SEQ ID NO 11
<211> LENGTH: 3854
<212> TYPE: DNA
<213> ORGANISM: Artificial Sequence
<220> FEATURE:
<223> OTHER INFORMATION: Synthetic: lipoxygenase-3

<400> SEQUENCE: 11

```
atgtcgattg attctgttcc agatattgcc tatgacggtg aagcgaaggt ggaaactgat    60
cctgatgttg ctgttcttac gacttccccg gcgtctcagt ctctatactc tcccgcaata   120
ctggcattcg ttcccaacca tgataaatct ttgctgcaac gattgtggtt gaatggagat   180
ggcatcaaat caacgtcaac tagagctctt gattacaaag tggccaaaaa ggttgctatg   240
accttgttgc acaatgacaa gcaacgttct ccattagtcg atcttcataa ccctgctgct   300
caattatcgt ccacacagta tcccttcaca cgaaaggtcg aaacaccact cgcctccacg   360
caaacaccag accctcaact tgtattccag cgtttgatgc aggagaacca tgtcgtcgag   420
catccgaatg gaatttcggg tctagctttt gttctcgcta ctgttatttc gctttctctc   480
atccgtatca acgaaaagaa accagaatgc aacgaaacgt ctccttatct tgatctatct   540
cccctctatg gtgtgaatga tgcagagacg gatatggttc gtgctaagga cgggcgcgga   600
atgctctctc cggattgttt ctacgaggac cgtgtcatgt tactcccacc cgcagtgtcc   660 gcattttga ttctttggaa cagaaatcac aatttcatcg cacgacttct tttgctgaat   720
aacgaaggaa acaaatgggt caaaccctct gacgatgcct tctcacctga tggtaacctc   780
gccgcgaacc tccaagcaca agacgacgag atcttcacca ttgcacgtct gataaactgt   840
gttcagttca agaacgttgt tgcagtggac ttcctaaaag tattgatggg gcttccacac   900 gacgaaaga gcgcagattt ggacatctca attgatcatg aacaattgga gaggggtaga   960
ggtcatgact ctagcatgga atctgctctt ctttataact ggacgtcaat gatagctaca  1020
gaagatgtca ggaaaatcga gaaacggtt gacgacgaat ttcacactac actcgatcag  1080
ctgtctgctg acgacgtgca gaacatgatg atgaatggta caaggaatcc ggatagacga  1140
taccgagaca gcgcaggcct caaacgcggg agagatggtc gcttccagga taatgatctt  1200
gctcgtgtcc tgcaagatgc gacaggatat catgcaggcg cgcccggcgc tcgtcgcatc  1260
ccctcatgct tccgcacctc tgaaatcatg attattgaac gagcgagacg gtggggcgta  1320
tgctctttca acgacttcag gaaattttta ggtctcaaag ttctaaagag cttccaagag  1380
tggaactcga accctgatgt tttcagggca gccgaggagc tctatggaag cattgacaac  1440
ttggaacttt atcctggcct ccaagctgag gacacatctg ggtccggtct tgggtttggt  1500
tgcacgatga cgtacggcct cttttgccgat attgtggcta taatgcgcag tgaccaccgt  1560
tttacgaccg aatttaccgc tggtaaatta actcaatggg gttacaatga ctgtactcgc  1620
cgtttgaata tggtgccttt cacctccacg ttgcctagat tattgcagcg aaattttcct  1680
cggaactatc catacgacaa cacctacagt ctgttcccct tgacctgtcc tgccacgacg  1740
aagacagcct tagccgattc gcgcaatcaa tacgatttcg agaggcccga agttcacaat  1800
gtcaaagtca tagagacgaa gagagcaata agttatgtct tcaacaaacc ctctgtatac  1860
caaacaatct atggcaagaa tctcgagaaa ttgacggacg ttatggctat ttcctgggt  1920 ttcgataacg aattgcttca tgatcgagat caaatgatga cactgtttgc actaattccg  1980
gacaaagggt ctttgtctcg acacgcatcc tatttcagta ctactgcggc tgcccttata  2040
agagacaaat cgatccaaaa caatgggcac aggtccgttg atatcgtacg agatgttatc  2100
aacacgacat gcactcgttg ggtatgcgag acactctgtg gacgctctct gtcagacggt  2160
gaggcgacaa aaagcatga agaattcgca gctatttatg catatatttt tcgaactatc  2220
gatcccgaga ctgggtgggc ggtccgtgaa gctgccatgg atgccagttc aagactcgga  2280
aaagatatcg aacgtcatct gcccatcccc tccgacatcg gaggcacaaa ctggatcaac  2340
```

```
gatttcagaa gctgtctcat agatctatat tcatggttca ctcgaatctg tcaagagatg    2400
ggacccggga aggaattaac acaccgcgtg gccttgacct ttcttgacag gatggtcaag    2460
tcgaacagac agttccgcct tggcgagctc accaaccacg gccatctccg agacatcatt    2520
gatgattcca atgtccagag ccagaagaa gcacttgaga agcgtcggat agtggcgaac     2580
gttttgggat tggctgtcgt tacggctgtc aactacgcac aaacatgtac acatgctgtt    2640
gatttttatc tcggcgatga acacgaagaa gaaaggaaag aaattgtacg actatcaatg    2700
ttgtcgccaa gagattcgcg gagccaaggc gcgaacaaga agatcatggg ttatattcgg    2760
gaagcacaaa gacttagcca gccattagga ctttggcgtg acgtcgtcga aaggacttc     2820 atcccacaag gaaacggtgt agaagtccgc aaaggggatc gtatctttgc tgacttcaat    2880
aaggctcata aaaatgccat ggacttctgt catcctaaca agatagaccc agatcggaaa    2940
actccttcca tacagggtat gggacttcac aaatgtcctg gtataggctt tgtagacgag    3000
actatgccag agctctttaa atctatcttt cgcttgaaga atcttcgacg tgacagtggc    3060
aaggccggcc gcttggagat gtttgttttgc caccctgcgc ctgcccagtc agatccaaag    3120
gtatatttag atcccactgg cgagatctct catttccctc gatctctttc tttgttgtat    3180
gacgatgatg gctctgcgga ggggtccccc tcaaagctga aaaagcggaa atggagagtc    3240
cttcctggga agaagactga gaaattacgg cgtaacatgg atcaagccat gcgagcttg     3300 gtagtggcga tctcccctgct attcatcctg ctccaaatgt ttcatgttta ttcccaccat   3360
atgccctcat tccgatttcc tttctcttcg acacctaaac gccgagaccc accgccatcg    3420
atgggtgata tcaaagtaga gtcgtagaa tgtccgacgc caacggaagt cttccaacca    3480
tatgagatcc atacgatgct cccaggttcc gacgggcatc cgattccact tgaatacacc    3540
atagaccacc ctaagccgca caagctgagt gtggtagaca tcgatgagcg ggacatgcag    3600
atggctgttt atgtagatga tgacctgaga ggactcacgc gggattcga actgaaccaa      3660 acgatgaact gcgggggagga tgtggcaaca tgttttgacga gtggattcag cgctggtgtt   3720
gttgtcgtac gacctggtaa acatacggtt aggatccagt gggtggggaa agactatata    3780
cctggtactc acgacatcga ctggggtaag gagcgaagcc ggcgtctgaa gtggcaacgg    3840
gagtactgtg ccat                                                       3854
```

<210> SEQ ID NO 12
<211> LENGTH: 1557
<212> TYPE: DNA
<213> ORGANISM: Artificial Sequence
<220> FEATURE:
<223> OTHER INFORMATION: Synthetic: Hydroperoxide lyase

<400> SEQUENCE: 12

```
atgtccctca agcattcttc cctctccgcc ttcatcccat cctccacttc acatcccccg      60
ctctacaatt ttccagtccc gtcttttctc aatatcaccg ggaaatcctt cacttggtta    120
tacaccaccc ttgcaatcgt ctttgctctt ctcgttctag agcagtcagt atatagatac    180
aagaaacgtc atttacctgg tgctaaatgg actattccta aatcggtaa attcgccgat     240 tccttgtcgc ctaccttgga agggtacaag aaacagtggg attcgggtcc tttgagcgct    300
gtcagtgtgt tcaacatttt cattgtcatg gcctcttcaa atgactatgc ccgcaaaatt    360
ctcaactctc ccggctttgc cgaaccatgt attgtacatg ccgccaagtc aatcctcctt    420
tctgacaatt gggtcttcct gaacggaaaa gctcatactt catatcgccg tgttcttaac    480
agtctcttca cccgccgtgc actcagcatt tatattccaa tcgaagaaaa cattacgcgt    540
```

```
aaacatttcg ccaaatggct cgcgactgct tccaaggaat ccgcgcctca gaccatcatg    600
atgactgtac gtcacttgaa tatggataca tcattgaacg tcttctgcgg taaacatatc    660
tcagaagagg ccgctctgga gatcaacgaa aagtactggg ccatcacgaa ggctcttgaa    720
cttgtaaact tcccgctcgc tctccctggc acgaaagttt ataatgccat ccaagcccgt    780
aaatctgccc tccattggtt ggagcttgca gccaacagaa gcaagaaggc tatggccaat    840
ggtgcagagc cccagtgcat gttagacgag tgggttcaga tactcaacga cccctcatat    900
aacggcaggc gggatttcag tgatctggaa atggccatgg tcctcttctc gttcctgttc    960
gcatcgcagg acgctctgag cagtgccgtg atttatgggt tccagcactt ggcagaccat   1020
cctgaagttc ttgccaaaat acgagaggag caagagaaag tccgccaggg cgattaccag   1080
aagcctctga cgctcgaaat gatcgatcaa atgacttacc tcaacgcagt tgttaaggag   1140
agcttgagaa tcaagccacc cgtcaccatg atcccgtaca aggccttgaa agctttccca   1200
atctctgacg actacgttgt accccctggc agcatggtca tcccttcgtt ctttaactct   1260
ttgcacgatc cctccgtcta ccccgaaccc gaaacgttta atcccgaccg ctggcttgat   1320
cctgaaagtt ctgcaaacca gaatcccaag aacttcattg gttttggcag tggcccacac   1380
cgctgtatcg gatttgagta tactttcata aacattgcta tcgtgcttgc gaccgccgct   1440
gtcacgatga acattgagca tgatgttacc cccctcagcg acaaagtcga gattatcgcg   1500
acactgtttc ccaaagacgg atgtcgtctc agattatcgc cacggacaca acatcca      1557
```